United States Patent [19]

Donaldson

[11] 4,334,090

[45] Jun. 8, 1982

[54] SLURRIES OF TEREPHTHALIC ACID IN ETHYLENE GLYCOL

[75] Inventor: Peter A. Donaldson, Yarm, England

[73] Assignee: Imperial Chemical Industries Limited, London, England

[21] Appl. No.: 208,348

[22] Filed: Nov. 19, 1980

[30] Foreign Application Priority Data

Nov. 28, 1979 [GB] United Kingdom ................. 7941092

[51] Int. Cl.$^3$ ....................... C07C 63/14; C07C 51/42
[52] U.S. Cl. ..................................... 562/480; 562/485
[58] Field of Search ............................... 562/485, 480

[56] References Cited

FOREIGN PATENT DOCUMENTS 54-20482  7/1979  Japan .................................. 562/485

*Primary Examiner*—Alan Siegel
*Attorney, Agent, or Firm*—Cushman, Darby & Cushman

[57] ABSTRACT

The viscosity of a slurry of terephthalic acid in ethylene glycol is reduced if the terephthalic acid is first submitted to mild attrition at an elevated temperature.

18 Claims, No Drawings

SLURRIES OF TEREPHTHALIC ACID IN ETHYLENE GLYCOL

The present invention relates to slurries of terephthalic acid in ethylene glycol.

Terephthalic acid and ethylene glycol are the starting materials for the manufacture of a synthetic polyester. In the preparation of the polyester the terephthalic acid and ethylene glycol are first reacted together to form a mixture of low molecular weight oligomers which are then polymerised further to the desired product.

In the past the terephthalic acid has been used in the reaction in the form of dimethylterephthalate but with the recent trend towards the production of highly pure terephthalic acid it has become possible to use the acid itself so reducing the overall costs of the process by dispensing with the methanol and the need to make dimethylterephthalate.

Terephthalic acid has a relatively low solubility in ethylene glycol so the first stage of the process involves the use of a slurry of terephthalic acid in ethylene glycol which has to have a sufficiently low viscosity for it to be handled e.g. to be transported by pumping but which preferably has a molar ratio of ethylene glycol to terephthalic acid as near as possible to 1:1. At ratios close to 1:1 however, the slurries are usually too viscous to be used.

It has been found that the physical form of the terephthalic acid has an important effect upon its slurryability characteristics and that terephthalic acid made by the same process but subjected to different purification procedures gives slurries having different viscosities despite having the same ratio of acid to glycol. In practice it is desirable to use as near as possible an equimolar proportion of terephthalic acid to ethylene glycol because an excess of ethylene glycol, besides giving rise to unnecessary handling procedures, tends to condense with itself to give diethylene glycol which then enters into the esterification reaction producing an inferior polymer. This self-condensation is catalysted by the acid and favoured by excess glycol. In commercial practice it has proved very difficult to work at a 1:1 molar ratio of terephthalic acid to ethylene glycol because the viscosity of such slurries is very high and it has been customary therefore to work at glycol to terephthalic acid ratios of 1.3 to 1.4:1. We have now found a method of treatment of terephthalic acid crystals which has the effect of improving their slurryability in ethylene glycol in the sense that the viscosity of the slurry for a given ratio of glycol to acid is reduced so enabling slurries containing a higher ratio of terephthalic acid to glycol to be used in the manufacture of the polyester. In addition, the slurries produced have an improved storage stability.

According to the invention the viscosity of a slurry of terephthalic acid in ethylene glycol is reduced by a method which comprises subjecting the terephthalic acid crystals before forming the slurry to mild attrition at an elevated temperature in the absence of a solvent for a period of time sufficient to modify the crystals so that they form a slurry with ethylene glycol which has a reduced viscosity.

The crystals are subjected to the process in a free flowing condition ie in the substantial absence of solvents such as water and acetic acid. The crystals may however be fed to the process in a "wet" condition ie containing some solvent from a previous process stage eg up to 15 weight % water or acetic acid. This solvent evaporates at the temperature of operation of the method ie the crystals are dried in situ.

Preferably the viscosity of the slurry is reduced to a value which is less than 30 poise more preferably less than 20 poise at a mole ratio of ethylene glycol to terephthalic acid of 1.40:1. This specified viscosity is determined using a Brookfield viscometer fitted with a number 3 spindle and working at a speed of 5 rpm. The method of determination consists of weighing a 100 gram sample of terephthalic acid into a 150 ml tall form beaker without a spout, adding 52.29 grams ethylene glycol, mixing to a slurry and then determining the viscosity at 24°±1° C. Three determinations are made and the slurry viscosity in poise is the mean of the three readings multiplied by two. It is important that the glycol should contain less than 1% by weight water as this factor has a critical effect upon the viscosity.

It is even more preferred that the method of the invention be operated so that the viscosity of the slurry is less than 50 poise at a mole ratio of ethylene glycol to terephthalic acid of 1.30:1 particularly less than 50 poise at a mole ratio of 1.15:1 and especially less than 100 poise at a mole ratio of 1.05:1. If desired, the method according to the invention may even be operated so that a handleable slurry (ie one with a viscosity of less than 100 poise) is obtained at an ethylene glycol to terephthalic acid mole ratio of 1:1. At these lower mole ratios ie 1.30:1, 1.15:1, 1.05:1 and 1.00:1 the viscosity determination should be carried out using the Brookfield viscometer as described in the preceding paragraph but working at a speed of 10 rpm and reducing the amount of glycol used to 48.55 grams (1.30:1), 42.95 grams (1.15:1), 39.22 grams (1.05:1) and 37.35 grams (1.00:1). At a speed of 10 rpm the mean of the three determinations gives the viscosity direct and does not need to be multiplied by two.

In chemical engineering practice attrition is generally considered to be a function of grinding and milling machines but we have found that such machines tend to be too severe in operation for the method of the present invention because, we believe, they cause substantial crystal breakdown and produce an undesirable amount of fine material. It is preferred therefore not to use the type of process in which the terephthalic acid crystals are subjected to pressure between cooperating grinding or crushing surfaces but instead to carry out the attrition in the type of machine conventionally used for mixing powders or for blending powders and liquids. The simplest form of such a machine comprises a container in which the crystals are agitated so that they rub one with another and with the walls of the container so working on the crystal surfaces to alter their profile and to cause some slight breakdown in crystal size. It is preferred that the agitation of the crystals is carried out in such a way that they are hurled and whirled around the vapour space inside the container in the form of a fluidised bed or a solid-gas dispersion. The atmosphere in the container is usually air but may be an inert gas eg nitrogen or dry, superheated steam, and in one form of the invention the agitation of the crystals may be induced by a gas circulation. In general we believe that sufficient energy should be imparted to an individual crystal by agitation so that it moves in the vapour space in the container but that the latter should contain a sufficient number of crystals for a crystal once set in motion to collide with another crystal as soon as possible. As the crystal surfaces soften at the temperature at which the method is operated, some agregation of particles is also believed to take place. The net effect of the process of attrition therefore is to change the profile of the crystal surfaces and the crystal particle size distribution.

The method according to the invention may advantageously be carried out in an apparatus which comprises a container provided with one or more rotating agitating elements eg paddles located inside the container. The agitating elements may be mounted on one or more shafts extending horizontally through the container and are preferably arranged perpendicularly and helically on the shafts. A preferred agitating element comprises an arm on which is mounted an impelling tool at the end opposite the shaft and adjacent the wall of the container. The impelling tool is preferably a single sided or double sided ploughshare more preferably the latter. The ploughshares may be used in a horizontal cylindrical container and are advantageously tapered in the direction of rotation of the agitating element and have symmetrically tapered outer surfaces which are convexedly curved about an axis extending longitudinally of the cylinder parallel to the cylinder axis, and side surfaces converging concavely and symmetrically inwardly from the tapering side edges of the outer surface towards the axis of rotation of the agitating element. The container, which is preferably a horizontal cylinder, may be stationary or may be rotatable and assemblies are provided to drive the agitating elements and, if necessary, the container.

A modification of the apparatus described in the preceding paragraph as being useful for carrying out the process according to the invention comprises arranging within the container one or more driven choppers to travel next to the wall of the container, the agitating elements continually moving terephthalic acid crystals to the chopper and the chopper continually returning the terephthalic acid to the working region of the agitating elements. The design of the chopper is not important ie it may be a single or multiple chopper and may comprise one or more cutters. It is preferred however that the cutter or chopper edges are blunt and that its speed of rotation be high compared with that of the agitating elements eg 2,000 to 5000 rpm.

The time for which the terephthalic acid crystals are subjected to the mild attrition is inter-related with the degree of attrition and the temperature, the more rapid the rate of attrition and/or the higher the temperature the less the time needed. Similarly, over a longer period of time the rate of attrition and/or the temperature may be reduced. Although times of up to 2 hours and preferably up to 1 hour may be used for batch operation it is preferred that the time taken for the method under continuous or semi-continuous operation is 10 to 50 minutes more preferably 20 to 40 minutes.

The temperature under which the process is operated is dependent upon time, as has been previously explained, and upon the rate of attrition. Suitably the temperature lies in the range 140° to 250° C. preferably 150° to 250° C. more preferably 160° to 220° C. particularly 190° to 210° C. Although temperatures higher than 250° C. may be used operation becomes more difficult due to sublimation of the terephthalic acid which becomes appreciable above 300° C.

One type of commercial mixer which we have found satisfactory in the practice of the invention is the so called ploughshare mixer manufactured by Morton Industrial mixers in the UK and Gebrüder Lödige Maschinenbau GmbH in Germany. In this type of machine, plough shaped mixing shovels are arranged at intervals on a horizontal shaft which rotates in a horizontal cylindrical container. The size, number, arrangement, geometric shape and peripheral speed of the mixing shovels are synchronised to force the material in the mixer into motion in three dimensions. The particles of the material collide with each other, with the wall of the drum and with the mixing elements. The abrasive effect is preferably enhanced by one or more separately driven, high speed, rotating choppers or multiple choppers which, in co-operation with the plough shaped mixing shovels increase the abrading effect. The choppers are situated in the lower half of the mixing container and in each case the drive shaft of the chopper enters the drum wall between the action zones of the adjacent plough shares. The mixer is provided with heating means, eg a jacket adapted to be heated by a heat transfer fluid such as steam.

In the following experiments the machine used was the "Multimix" machine ("Multimix" is a trade mark) manufactured by the Morton Machine Company Limited which worked on the principles described in the preceding paragraph. It should be understood however that this is only one type of machine which may be used to put the present invention into practice and it is not intended to be in any way limiting.

EXPERIMENTAL METHOD

The Morton "Multimix" is a ploughshare mixer which was fitted with one multibladed chopper. The machine comprised a horizontal shaft mounted centrally and rotating in a horizontal cylindrical container of total capacity 50 liters. Two ploughshare shaped shovels were fixed to the shaft by arms arranged at 180° to each other. The shaft rotated at 180 rpm. The machine was operated with a content of terephthalic acid crystals of approximately 50 to 60% of the total volume. The chopper was separately driven at 2,900 rpm and was mounted through the side of the drum at right angles to the direction of rotation of the ploughshares. The inside of the drum was made of stainless steel and was heated by means of steam supplied to an encircling jacket.

In operation 15 to 25 kg of dry terephthalic acid crystals were supplied to the machine and samples were removed at intervals by stopping the machine. The samples were tested for slurry viscosity using a Brookfield RVT machine by the method described earlier in this specification. During the experiments the temperature of the contents of the machine was measured by means of a portable "Digitherm" ("Digitherm" is a trade mark).

RESULTS

The improvement in slurry viscosity to be obtained using the process according to the invention is shown by the following comparative tests in which two samples of commercial terephthalic acid were used. The samples were treated in the Morton "Multimix" machine at 150° C. for 60 mins. and were then made up into slurries of varying molar proportion of terephthalic acid to ethylene glycol and their viscosities measured. The same measurements were made on comparative samples which had not been treated in the "Multimix" machine. The results were as follows:

| Sample | Slurry Viscosity (poise) at ethylene glycol/terephthalic acid molar ratio | | | |
|---|---|---|---|---|
| | 1.38:1* | 1.30:1 | 1.15:1 | 1.05:1 |
| A | 29 | 26.5 | 55 | 89 |
| A comparative | 51 | >100 | >100 | |
| B | 25 | 44 | 100 | >100 |
| B comparative | >200 | | | |

*The viscometer speed of rotation was 5 rpm in this test as opposed to 10 rpm in all the other tests.

A second series of experiments examined the effect of temperature and time on the method according to the invention. Commercial samples of terephthalic acid from two different sources served as the test material and each was submitted to processing in the "Multimix" machine at different temperatures for different times. The slurry viscosities were measured by the specified method the results being as follows:

| | SAMPLE C | |
|---|---|---|
| | Viscosity at 1.38:1* at Temperature °C. | |
| Time (mins) | 150–156 | 138–157 |
| 0 | >200 | >200 |
| 5 | 100 | 92 |
| 10 | 69 | 79 |
| 20 | 52 | 53 |
| 30 | 30 | 44 |

| | SAMPLE D | | |
|---|---|---|---|
| | Viscosity at 1.38:1* at Temperature °C. | | |
| Time (mins) | 142–155 | 90–148 | Ambient |
| 0 | 52 | | 61 |
| 1 | | 52 | 58 |
| 3 | | 48 | 54 |
| 5 | | 44 | 53 |
| 7 | 36 | | |
| 10 | | 36 | 57 |
| 12 | 31 | | |
| 15 | | 34 | 62 |
| 17 | 24 | | |
| 27 | 24 | | |

*Spindle speed 5 rpm

These results show in general that the improvement in viscosity increases with temperature and time under standard conditions of attrition although there are indications that under given conditions of attrition and temperature a time is reached after which no further improvement occurs.

The machine used in the above series of experiments had one chopper. For commercial practice however a machine has been designed which has up to eight multiple choppers adapted so that two or more of the choppers are located between a pair of ploughshares eg two to eight choppers radially disposed between one pair of ploughshares. This machine is also provided with heating means enabling its contents to be heated at temperature up to 250° C.

A continuous machine akin to that described in the preceding paragraph for commercial operation comprised 4 multiple choppers located between pairs of rotating ploughshares. There were 7 ploughshares in all. The ploughshares and cutters were mounted as described above in a horizontal stainless steel cylindrical container of 300 liters capacity heated by a steam jacket and with a thermometer permanently inserted through the cylinder wall to measure the temperature of the contents. The ploughshares rotated at 155 rpm and the choppers at 2900 rpm. Terephthalic acid crystals, preheated to 140° C., were continuously fed to the top of one end of the cylinder and product continuously withdrawn by means of a weir from the top of the opposite end. At any one time the cylinder contained 200 kg of terephthalic acid and residence time in the cylinder was 20 to 30 minutes.

Samples of terephthalic acid from the same source were treated at different temperatures using this apparatus described above, the slurry viscosities obtained being as follows:

| Temperature | Viscosity at 1.05:1 molar ratio (poise) |
|---|---|
| 143 to 150° C. | 98 |
| 170 to 173° C. | 89 |
| 192 to 196° C. | 65 |
| 198 to 200° C. | 50 |

I claim:

1. A method of reducing the viscosity of a slurry of terephthalic acid in ethylene glycol which comprises subjecting the terephthalic acid crystals before forming the slurry to mild attrition at an elevated temperature in the absence of a solvent for a period of time sufficient to modify the crystals so that they form a slurry with ethylene glycol which has a reduced viscosity.

2. A method according to claim 1 in which the viscosity is reduced to a value of less than 30 poise at a mole ratio of ethylene glycol to terephthalic acid in the slurry of 1.40:1.

3. A method according to claim 2 in which the viscosity is reduced to a value of less than 20 poise at a mole ratio of ethylene glycol to terephthalic acid in the slurry of 1.40:1.

4. A method according to claim 1 in which the viscosity is reduced to a value of less than 100 poise at a mole ratio of ethylene glycol to terephthalic acid in the slurry of 1.05:1.

5. A method according to claim 1 in which the viscosity is reduced to a value of less than 100 poise at a mole ratio of ethylene glycol to terephthalic acid in the slurry of 1:1.

6. A method according to claim 1 in which the terephthalic acid crystals are submitted to mild attrition by agitation in a container so that the crystals rub one with another and with the walls of the container but in which the crystals are not subjected to pressure between cooperating grinding or crushing surfaces.

7. A method according to claim 6 in which the terephthalic acid crystals are agitated in such a way that they are hurled and whirled around the vapour space in the container in the form of a fluidised bed or a solid-gas dispersion.

8. A method according to claim 6 or claim 7 in which the container is a horizontal cylinder which is stationary or capable of revolution and which comprises one or more shafts extending through the cylinder and agitating elements fixed to the shaft and extending therefrom in the direction of the wall of the cylinder.

9. A method according to claim 8 in which the agitating elements comprise paddles.

10. A method according to claim 8 in which the agitating elements are arranged perpendicularly and helically on the shaft and comprise arms with impelling tools on their ends.

11. A method according to claim 10 in which the impelling tool is a single-sided or double-sided ploughshare.

12. A method according to claim 11 in which the container is a horizontal cylinder and the ploughshares are tapered in the direction of rotation of the agitating elements and have symmetrically tapered outer surfaces which are convexedly curved about an axis extending longitudinally of the cylinder parallel to the cylinder axis and side surfaces converging concavely and symmetrically inwardly from the tapering side edges of the outer surface towards the axis of rotation of the agitating elements.

13. A method according to claim 8 in which the terephthalic acid crystals are agitated by means of said agitating elements cooperating with at least one driven chopper arranged inside the container to travel next to the wall of the container the agitating elements continually moving terephthalic acid crystals to the chopper and the chopper continually returning the terephthalic acid to the working region of the agitating elements.

14. A method according to any one of the preceding claims which is carried out at a temperature of 140° to 250° C.

15. A method according to claim 18 which is carried out at a temperature of 190° to 210° C.

16. A method according to any one of the preceding claims in which the period of time sufficient to modify the crystals is up to 2 hours.

17. A method according to claim 20 in which the time is up to 1 hour.

18. A method of reducing the viscosity of a slurry of terephthalic acid in ethylene glycol which comprises treating the terephthalic acid crystals before forming the slurry by agitating them in a container at a temperature in the range 140° to 250° C. for a period of time up to 2 hours in which the crystals are hurled and whirled around the vapour space in the container in the form of a fluidised bed or a solid-gas dispersion and in which the viscosity of the product terephthalic acid crystals in a slurry in ethylene glycol at a 1.40:1 molar ratio glycol to terephthalic acid is less than 30 poise.

* * * * *